(12) United States Patent
King

(10) Patent No.: US 7,217,937 B2
(45) Date of Patent: May 15, 2007

(54) AUTOMATIC IDENTIFICATION OF SUSPENDED PARTICLES

(75) Inventor: Frederick David King, Richmond (CA)

(73) Assignee: Brightwell Technologies, Ottawa, Ontario (CA)

( * ) Notice: Subject to any disclaimer, the term of this patent is extended or adjusted under 35 U.S.C. 154(b) by 254 days.

(21) Appl. No.: 10/990,490

(22) Filed: Nov. 18, 2004

(65) Prior Publication Data

US 2005/0109950 A1 May 26, 2005

Related U.S. Application Data

(60) Provisional application No. 60/523,677, filed on Nov. 21, 2003.

(51) Int. Cl.
*G01J 1/58* (2006.01)
*G01N 21/64* (2006.01)

(52) U.S. Cl. ................. 250/458.1; 250/461.2; 250/459.1; 356/335

(58) Field of Classification Search ......... 250/458.1, 250/459.1, 461.1, 461.2; 356/72, 335, 336
See application file for complete search history.

(56) References Cited

U.S. PATENT DOCUMENTS

| | | | | |
|---|---|---|---|---|
| 5,260,764 A | * | 11/1993 | Fukuda et al. ............... 356/73 |
| 5,633,503 A | * | 5/1997 | Kosaka ..................... 250/458.1 |
| 5,663,057 A | * | 9/1997 | Drocourt et al. ............ 435/40.5 |
| 5,805,342 A | * | 9/1998 | Gravely ..................... 359/618 |
| 5,825,477 A | * | 10/1998 | Furuie ......................... 356/72 |
| 5,973,330 A | * | 10/1999 | Hayashi .................... 250/458.1 |
| 6,139,800 A | | 10/2000 | Chandler ................. 422/82.08 |
| 6,507,400 B1 | * | 1/2003 | Pina et al. ................... 356/338 |
| 6,549,275 B1 | | 4/2003 | Cabuz et al. ................ 356/39 |
| 6,959,618 B1 | * | 11/2005 | Larsen ...................... 73/865.5 |
| 6,970,246 B2 | * | 11/2005 | Hansen ....................... 356/417 |
| 2002/0071121 A1 | * | 6/2002 | Ortyn et al. ................ 356/419 |
| 2003/0100024 A1 | * | 5/2003 | Cassells et al. ............. 435/7.2 |
| 2004/0157211 A1 | * | 8/2004 | Skyggebjerg et al. .......... 435/5 |

* cited by examiner

*Primary Examiner*—Albert Gagliardi
(74) *Attorney, Agent, or Firm*—Teitelbaum & MacLean; Neil Teitelbaum; Doug MacLean

(57) ABSTRACT

The present invention relates to the automatic analysis and identification of different species of particles in a liquid sample using both fluorescent tagging and magnification techniques. A light source at a first wavelength is used to induce the tagged particles to emit light at a second wavelength, while the image thereof is captured on a pixel array of a digital camera. A second camera can be used to capture an image of the particles illuminated at the first wavelength, which is separated from the second wavelength by an optical filter. Alternatively, a second light source emitting pulses of light at the second wavelength, which alternate with the first light source.

20 Claims, 1 Drawing Sheet

AUTOMATIC IDENTIFICATION OF SUSPENDED PARTICLES

CROSS-REFERENCE TO RELATED APPLICATIONS

The present invention claims priority from U.S. Patent Application No. 60/523,677 filed Nov. 21, 2004, which is incorporated herein by reference.

TECHNICAL FIELD

The present invention relates to a method and apparatus for automatically identifying and counting sub-populations of species within an overall population contained within a flowing stream of transparent liquid, and in particular to particle species identification through a combination of fluorescent tagging and detection and, automated image analysis.

BACKGROUND OF THE INVENTION

Suspended particle populations found in the water, environmental and medical applications are often composed of many different inorganic, organic and mixed sub-populations. Among these, certain biological species are of particular concern as indicators of pathogen presence or of contamination.

Fluorescent tagging methods are commonly used to identify and count biological species. Fluorescent tags (also called probes) are fluorescent materials, which attach selectively to the entity of interest. Since the amount of the probe which is attached to a single entity, e.g. a bacteria, is small, the fluorescence intensity which can be obtained from one bacteria is also small. In standard methods, the sample is filtered, the filter is placed in a growth medium for the target species, and incubated for many hours allowing the live species to multiply to colonies having a sufficient number of bacteria. The fluorescent probe when applied will attach only to colonies of the target species, which colonies, when present, are observed using fluorescence microscopy, either visually or with a camera, and counted.

Because of the time required for incubation, and because many species can't be cultured, alternative methods attempt to identify and count single target species without the multiplication step.

One method is to apply the fluorescent probe to the sample before or after filtering using a flat filter suitable for microscopic examination. The filter is placed in a fluorescence microscope and illuminated at the fluorescence pumping wavelength. Fluorescent emission of the target species, as identified by an operator either visually or by means of a camera, is used for identification and counting. Provided the microscope is suitably equipped, manual microscopic techniques also allow non-fluorescent images of the same particles to be collected. Unfortunately, these methods are still relatively slow, i.e. taking seconds per particle.

Automatic instruments, which can be used to identify and count sample particles, are of significant practical importance because microscopic analysis requires high skill level and is extremely time consuming, particularly when the concentration of the target species within the overall population is small.

In a conventional automatic instrument, the filter is automatically scanned with an intense optical beam at the probe absorption wavelength. A fluorescence detection system simultaneously examines the point of illumination and detects and counts any fluorescent particles.

U.S. Pat. No. 6,139,800 issued Oct. 31, 2000 to Chandler, and U.S. Pat. No. 6,549,275, issued Apr. 15, 2003 to Cabuz et al disclose another method commonly used to achieve species identification, i.e. flow cytometry, e.g. flow microfluorimetry or flow cytofluorometry. Flow cytometry includes a labeling step, in which target entities within the mixed population are tagged with one or several fluorescent probe compounds that selectively attach only to the target entities. The total particle population is suspended in a transparent liquid carrier. The sampling system is designed so that the particles pass, one at a time, through a small optical excitation zone, which is illuminated with one or more wavelengths. In order to maximize the number of particles analyzed, rapid flow rates of sample liquid are used, e.g. approximately 1 meter per second. Based on measurements of the characteristic scattering and fluorescent light "signature" of each particle, the instrument attempts to identify and resolve the total population into subpopulations. Flow cytometry identifies and classifies particles based on only three parameters, i.e. forward scattering, which represents particle size; side scattering, which represents a combination of surface properties and internal structure; and the presence or absence of a tag attached to the particle. This technique only works well if each of the target particles provides resolvably different signals for one or more of these measurements.

A number of limitations exist with fluorescence tagging methods in the analysis of natural samples, including: selective fluorescent probes are not available or possible for all species; the target entity may not provide a sufficiently distinct optical fluorescence and scattering signature for differentiating from other species; and there may be difficulties in preventing the fluorescent probe compound from attaching to one or more of the wide variety of species, other than the target species, contained within such samples. As a consequence, additional sophisticated techniques, such as immuno-magnetic separation, are required to concentrate the target species before fluorescence analysis is performed.

While flow cytometry does utilize particle morphology information, as derived from scattering signals, the information contained in these signals is limited, especially for particles greater than approximately 5 microns. An alternative existing technology uses only morphological information, derived from image analysis, to differentiate particles. Instruments, which use this method, route samples through a flow cell where a digital camera captures high quality images of each particle on a pixel array. Unfortunately, depth positioning of the particles must be within a few microns, because the allowed depth of focus is very small for high-magnification, high-quality images, typically 3.5 microns for a X10 objective. The system software attempts to classify each particle based on morphological characteristics such as shape, contrast or color. This method can be successful only if the sub-populations of interest are sufficiently different in these characteristics to be resolved by the instrument.

Manual microscopic techniques enable both fluorescent and non-fluorescent images of individual particles to be used in particle identification; however, automatic techniques, which use both types of images, do not exist. Up until now, considerable limitations in the processing rate and system design, which a simultaneous requirement for high quality image formation would normally impose, have prevented such a system from existing. For example: recording and analyzing the signals from each of a large number of detectors, e.g. a minimum of 200 pixels in an array used for high quality imaging, requires much more time than that required to detect and process signals from a small number of individual detectors used for fluorescence and scattering analysis. Furthermore, for accurate image formation, the particle velocity must be sufficiently low so that no significant motion takes place during exposure. Both of these factors limit the rate of particle analysis much below the rate, which can be employed for fluorescence and scattering analysis alone.

Moreover, in order to form a highly magnified image of a particle using standard microscopic techniques, the particle must be located with much higher precision than that required for fluorescence and scattering analysis, because the particle must lie within the depth of focus of the magnification system, e.g. 3.5 microns for a X10 objective. The sample capillary must also provide a clear undistorted optical path with the sample flow placed, with micron accuracy, at the best working distance of the magnification system. These requirements impose significant restrictions on instrument design, which will further reduce performance in the fluorescence and scattering mode relative to an instrument designed solely for this mode.

An object of the present invention is to overcome the shortcomings of the prior art by providing an automatic particle detection system utilizing both fluorescent and non-fluorescent images of individual particles, which are used to measure a larger number of parameters for each particle.

SUMMARY OF THE INVENTION

Accordingly, the present invention relates to a method for analyzing a liquid sample to differentiate and count particles of different species in an overall population, comprising the steps of:

tagging particles in certain species with a fluorescent material;

passing the liquid sample through a sample cell a portion at a time;

illuminating the sample cell with a first optical source having a wavelength and intensity $\lambda_1$, which causes tagged particles to emit fluorescent signals at a fluorescent wavelength $\lambda_2$;

separating the light exiting the sample cell into the optical source wavelength $\lambda_1$ and the fluorescent wavelength $\lambda_2$ using a wavelength selective filter;

forming a first image of the tagged particles in the sample cell with the light having the fluorescent wavelength $\lambda_2$ exiting the sample cell using a first magnification system on a first pixel array;

forming a second image of each portion of the liquid sample in the sample cell with the light having the optical source wavelength $\lambda_1$ exiting the sample cell using a second magnification system on a second pixel array or with light periodically illuminating the sample cell from a second light source at the fluorescent wavelength $\lambda_2$ using the first magnification system on the first pixel array synchronized with the second light source;

determining at least two parameters of a particle in each image;

correlating the parameters from the first image and the second image to differentiate and count the number of particles in each different species in the sample cell; and calculating the number of particles in each different species in the overall population.

Another aspect of the present invention relates to a device for analyzing a liquid sample to differentiate and count particles of different species in an overall population, comprising:

tagging means for tagging particles of certain species with a fluorescent material;

a sample cell through which the liquid sample flows a portion at a time;

a first optical source for emitting light having a wavelength $\lambda_1$ and an intensity, which will cause tagged particles to emit fluorescent signals at a fluorescent wavelength $\lambda_2$;

a wavelength selective filter for separating light emitted from the sample cell into the source wavelength $\lambda_1$ and the fluorescent wavelength $\lambda_2$;

a first imaging means for receiving the fluorescent wavelength $\lambda_2$ and for forming a first image of the tagged particles in the sample cell;

a second imaging means for receiving light at the emitted source wavelength $\lambda_1$ or for receiving light from a second optical source proximate the fluorescent wavelength $\lambda_2$, and for forming a second image for each portion of the liquid sample in the sample cell; and computing means for determining at least four parameters of the particles from the first and second images, and for correlating the parameters from the first and second images for each portion of the liquid sample to differentiate and count the number of particles in each different species in the sample cell and in the overall population.

BRIEF DESCRIPTION OF THE DRAWINGS

The invention will be described in greater detail with reference to the accompanying drawings which represent preferred embodiments thereof, wherein.

DETAILED DESCRIPTION

The present invention is based on the recognition that a digital optical imaging system can derive significant morphological information for a particle even when the system is operated under optical conditions such that the image contains levels of distortion, which would be unacceptable using conventional visual techniques. Specifically, the system can be operated: a) using a smaller number of pixels, e.g. 9 to 200, preferably 15 to 100, than that conventionally used for high quality imaging, thereby increasing processing speed; b) employing diffraction enlargement of particles, thereby allowing a reduction in the magnification and an increase in the depth of field, which relaxes the requirement for precise positioning of a particle or allowing multiple particles to be imaged simultaneously; c) employing particle velocities, which give rise to a finite degree of streaking; and d) employing a sample depth, which allows some particles to be partially out-of-focus.

Figure 1:
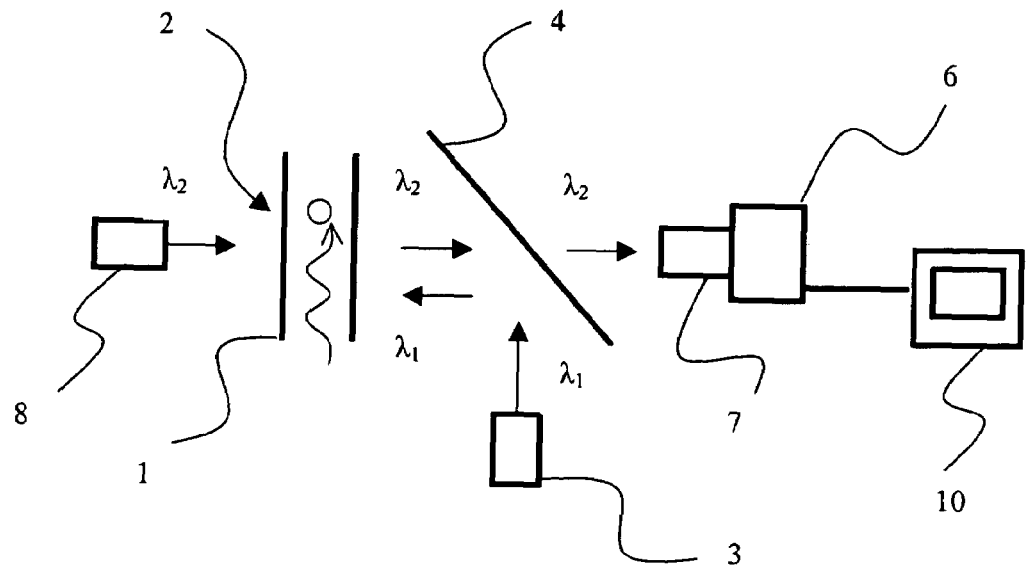
FIG. 1 is a schematic representation of an embodiment of the present invention.

A first embodiment of the present invention, illustrated in FIG. 1, includes a sample cell 1, which enables particles suspended in a clear liquid to pass either one at a time or in a three dimensional array through an optical excitation zone 2, preferably at laminar flow. Initially, a fluorescent tagging procedure is used to label any fluorescence target species present in the sample. A first light source 3 emits a first pulse of light at wavelength $\lambda_1$, which reflects off of optical filter 4 into the optical excitation zone 2. Any fluorescently tagged particles in the excitation zone 2 will then emit light at a fluorescence emission wavelength $\lambda_2$, which passes through the optical filter 4 to the digital camera 6. The optical filter 4 permits only a narrow band of wavelengths at or near the fluorescent wavelength $\lambda_2$ to pass to the digital camera 6. A magnification system 7 is provided for forming a clearer image on the pixel array of the camera 6. The number, intensity and location of pixels, which detect fluorescent signals are recorded by system software. At alternating periods of time a second light source 8 emits a second pulse of light at wavelength $\lambda_2$, i.e. within the bandpass of the optical filter 4 but outside the range of wavelengths that will induce fluorescence from the particles. As a result, any particle having adequate contrast will produce an image on the pixel array in the digital camera 6. During continuous work, the pulsing light sources 3 and 8 are synchronized with the digital camera 6. The number, intensity and location of pixels, which detect signals are also recorded by the system software in computerized control 10.

Each of the images is measured with respect to several parameters, e.g. area, maximum dimension, minimum dimension, perimeter length, circularity, average contrast, contrast variation, sphericity, Aspect Ratio, Perimeter, Heywood Diameter (smallest circle enclosing the particle), Feret Diameter, Convex Perimeter, Roughness, and Fractal Dimension. At least four parameters are measured; however, six, eight, ten, even sixteen different parameters can be measured. Since a larger number of parameters are measured, the chance of obtaining a unique particle signature is increased. As the image becomes more complex, the number of parameters becomes larger. The newly acquired images may also be compared to stored images of known particles using established image comparison/recognition techniques.

Subsequently, the measured parameters from the first image and the second image are correlated to differentiate and count the number of particles in each different species in the sample cell, and the number of particles in each different species in the overall population can then be calculated.

Figure 2:
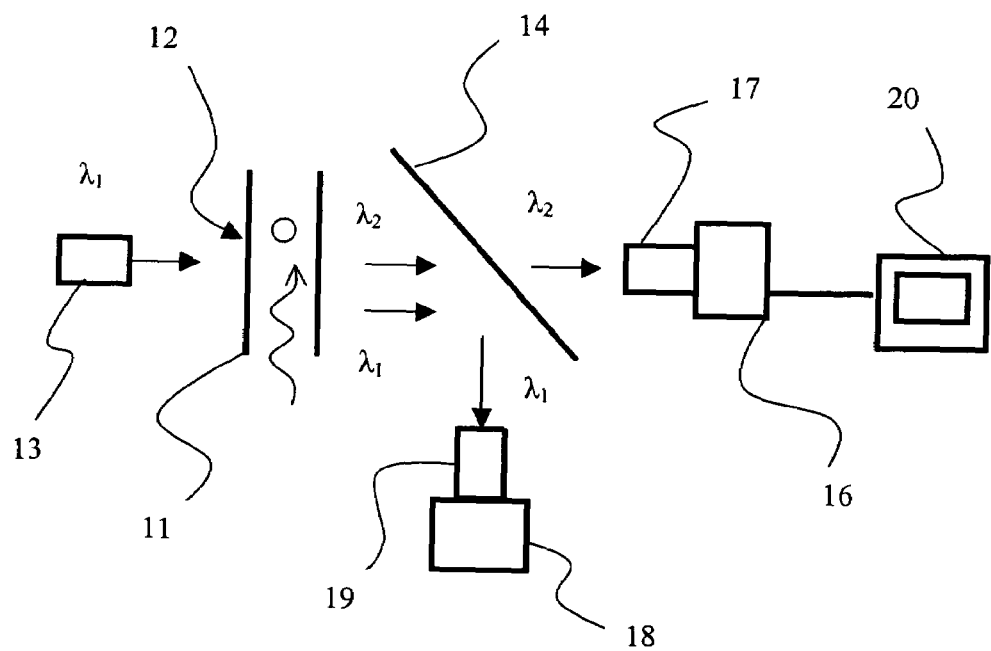
FIG. 2 is a schematic representation of an alternative embodiment of the present invention.

With reference to FIG. 2, a single light source 13 continually emits pulses of light at a first wavelength $\lambda_1$ at an optical excitation zone 12 of a sample cell 11. The fluorescently tagged particles absorb some of the light at $\lambda_1$ and emit light at the fluorescence emision wavelength $\lambda_2$. The fluorescence emision wavelength $\lambda_2$ passes through an optical filter 14, similar to optical filter 4 above, to a first digital camera 16 via a magnification system 17. The remaining light at the firsts wavelength $\lambda_1$ is reflected off of the optical filter 14 to a second digital camera 18 via a second magnification system 19. If the cameras have electronic shutters, the light source 13 could simply emit light continually. As above, the number, intensity and location of pixels, which detect fluorescent and not fluorescent signals on first and second images in the first and second cameras 16 and 18, respectively, are recorded by the system software in the computerized control 20.

The system software applies correction factors to compensate for pixellation effects, diffraction enlargement, out-of-focus enlargement and streaking. The fluorescence pattern (if present) and corrected image pattern of each particle are correlated by the system software and used to differentiate and count different species within the overall population.

Diffraction degrades visible images and is usually minimized as much as possible in microscopy by using the largest numerical aperture consistent with the linear magnification, which is required to produce a sufficiently large image of the smallest particle to be measured. However, by using a low numerical aperture, diffraction enlargement can be used to increase the size of an image of a particle and thereby the number of pixels it occupies. Accordingly, a lower level linear magnification can be used, thereby greatly increases the depth of field and field of view, which increases the number of particles that can be analyzed in an acceptable time period.

Since the velocity of the particles and the image exposure of the camera will be known, the degree of streaking, i.e. motion during image exposure time, can be calculated. Accordingly, system software can calculate the degree of streaking in recorded images, and correct the parameter calculations to compensate for the streaking effect, e.g. decrease the particle size calculation in accordance with error caused by the streaking effect. Preferably, the streaking component is not more that 50% more than the parameter being measured.

Captured images that are partly out-of-focus are corrected by the system software to eliminate the out-of-focus effects, which lead to errors in specific parameter calculations, e.g. increase perimeter measurement for particles beyond focal plane of camera. Preferably, the out-of-focus component is not more than 50% of the parameter being measured.

As above, the measured parameters from the first image and the second image are correlated to differentiate and count the number of particles in each different species in the sample cell and the number of particles in each different species in the overall population can then be calculated.

The optical resolution of the image will depend on the magnification value and numerical aperture of the optical magnification system, and on the depth of the optical sampling volume. A tradeoff exists between image quality and the rate at which particles may be analyzed. Normally, in order to maximize analysis rate, the system will be operated with the minimum resolution required to differentiate images of the target species.

The morphological information obtained by imaging is much more comprehensive that that obtained by scattering. The more comprehensive information provides a higher probability for differentiating and identifying a particle, particularly for larger particles with distinct features and those not amenable to unique fluorescence tagging.

Particles, which have fluorescent emission, will also provide images. This image data may be used to assist in eliminating particles, other than target particles, to which the fluorescent probes have inadvertently attached.

I claim:

1. A method for analyzing a liquid sample to differentiate and count particles of different species in an overall population, comprising the steps of:
    a) tagging particles in certain species with a fluorescent material;
    b) passing the liquid sample through a sample cell a portion at a time;
    c) illuminating the sample cell with a first optical source having a wavelength and intensity $\lambda_1$, which causes tagged particles to emit fluorescent signals at a fluorescent wavelength $\lambda_2$;
    d) separating the light exiting the sample cell into the optical source wavelength $\lambda_1$ and the fluorescent wavelength $\lambda_2$ using a wavelength selective filter;
    e) forming a first image of the tagged particles in the sample cell with the light having the fluorescent wavelength $\lambda_2$ exiting the sample cell using a first magnification system on a first pixel array;
    f) forming a second image of each portion of the liquid sample in the sample cell with the light having the optical source wavelength $\lambda_1$ exiting the sample cell using a second magnification system on a second pixel array or with light periodically illuminating the sample cell from a second light source at the fluorescent wavelength $\lambda_2$ using the first magnification system on the first pixel array synchronized with the second light source;

g) determining at least two morphological parameters of a particle in each image; and h) correlating the morphological parameters from the first image and the second image to differentiate and count the number of particles in each different species in the sample cell and in the overall population.

2. The method according to claim 1, wherein step c) includes reflecting light from the first optical source off of the wavelength selective filter to the sample cell; and wherein step f) includes periodically illuminating the sample cell with the second light source, whereby the light passes through the sample cell and the wavelength selective filter to the first pixel array.

3. The method according to claim 2, wherein step c) includes providing short pulses of light synchronized with step e), whereby steps e) and f) alternate for the liquid sample.

4. The method according to claim 1, wherein step c) includes passing light from the first optical source through the sample cell, whereby the fluorescent signals pass through the wavelength selective filter to the first pixel array; and wherein step f) includes passing light from the first optical source through the sample cell, whereby the light reflects off of the wavelength selective filter to the second pixel array.

5. The method according to claim 4, wherein step c) includes providing continuous illumination from the first optical source; and wherein step e) includes periodically exposing the first pixel array to the first optical source.

6. The method according to claim 1, wherein steps e) and f) include applying correction factors to compensate for one or more effects selected from the group comprising: pixelation effects, diffraction enlargement, out-of-focus enlargement, and streaking.

7. The method according to claim 1, wherein step g) includes measuring at least four of the morphological parameters selected from the group consisting of: area, maximum dimension, minimum dimension, perimeter length, circularity, average contrast, contrast variation, sphericity, aspect ratio, perimeter, Heywood diameter, Feret diameter, convex perimeter, roughness, and fractal dimension.

8. The method according to claim 1, wherein step g) includes determining at least six morphological parameters of each particle.

9. The method according to claim 1, wherein step b) includes: passing particles through the sample cell one at a time or in a three-dimensional array.

10. A device for analyzing a liquid sample to differentiate and count particles of different species in an overall population, comprising:

tagging means for tagging particles of certain species with a fluorescent material;

a sample cell through which the liquid sample flows a portion at a time;

a first optical source for emitting light having a wavelength $\lambda_1$ and an intensity, which will cause tagged particles to emit fluorescent signals at a fluorescent wavelength $\lambda 2$;

a wavelength selective filter for separating light emitted from the sample cell into the source wavelength $\lambda_1$ and the fluorescent wavelength $\lambda_2$;

a first imaging means for receiving the fluorescent wavelength $\lambda_2$ and for forming a first image of the tagged particles in the sample cell;

a second imaging means for receiving light at the emitted source wavelength $\lambda_1$ or for receiving light from a second optical source proximate the fluorescent wavelength $\lambda_2$, and for forming a second image for each portion of the liquid sample in the sample cell; and computing means for determining at least four morphological parameters of the particles from the first and second images, and for correlating the morphological parameters from the first and second images for each portion of the liquid sample to differentiate and count the number of particles in each different species in the sample cell and in the overall population.

11. The device according to claim 10, wherein the first and second imaging means includes a same first camera with a first pixel array; wherein pulses of light from the first optical source reflects off of the wavelength selective filter to the sample cell, whereby the fluorescent signals pass through the wavelength selective filter to the first camera synchronized with the first optical source; and wherein pulses of light from the second light source passes through the sample cell and the wavelength selective filter to the first camera synchronized with the second light source.

12. The device according to claim 11, wherein the first pixel array has 15 to 200 pixels.

13. The device according to claim 10, wherein the first and second imaging means comprises first and second cameras, respectively, with first and second pixel arrays, respectively; wherein light from the first optical source passes through the sample cell, whereby the fluorescent signals pass through the wavelength selective filter to the first pixel array; and wherein light from the first optical source passes through the sample cell, whereby the light reflects off of the wavelength selective filter to the second pixel array.

14. The device according to claim 13, wherein the first pixel array has 15 to 200 pixels.

15. The device according to claim 13, wherein the first optical source provides continuous illumination; and wherein the first camera includes shutter means for periodically exposing the first pixel array to the first optical source.

16. The device according to claim 10, wherein the computing means measures at least four of the morphological parameters selected from the group consisting of: area, maximum dimension, minimum dimension, perimeter length, circularity, average contrast, contrast variation, circularity, average contrast, contrast variation, sphericity, aspect ratio, perimeter, Heywood diameter, Feret diameter, convex perimeter, roughness, and fractal dimension.

17. The device according to claim 10, wherein the computing means applies correction factors to compensate for one or more effects selected from the group comprising: pixelation effects, diffraction enlargement, out-of-focus enlargement, and streaking.

18. The device according to claim 10, wherein the liquid sample is passed through the sample cell in a laminar flow.

19. The device according to claim 10, wherein the particles pass through the sample cell one at a time or in a three-dimensional array.

20. The device according to claim 10, wherein the computing means determines at least eight morphological parameters of each particle.

* * * * *